United States Patent [19]

Hughes

[11] Patent Number: 5,233,036
[45] Date of Patent: Aug. 3, 1993

[54] RAPAMYCIN ALKOXYESTERS

[75] Inventor: Philip F. Hughes, Hopewell, N.J.

[73] Assignee: American Home Products Corporation, New York, N.Y.

[21] Appl. No.: 839,653

[22] Filed: Feb. 20, 1992

Related U.S. Application Data

[63] Continuation of Ser. No. 598,270, Oct. 16, 1990, abandoned.

[51] Int. Cl.$^5$ .................. C07D 269/00; A61K 31/33
[52] U.S. Cl. .................................................. 540/455
[58] Field of Search ..................... 540/455; 514/183

[56] References Cited

U.S. PATENT DOCUMENTS

| | | | |
|---|---|---|---|
| 3,929,992 | 12/1975 | Sehgal et al. | 424/122 |
| 3,993,749 | 11/1976 | Sehgal et al. | 424/122 |
| 4,316,885 | 2/1982 | Rakhit et al. | 424/122 |
| 4,401,653 | 4/1983 | Maruyama et al. | 424/122 |
| 4,650,803 | 3/1987 | Stella et al. | 546/90 |
| 4,885,171 | 12/1989 | Sehgal et al. | 424/122 |
| 4,929,611 | 5/1990 | Okuhava | 514/183 |

OTHER PUBLICATIONS

Can. J. Physiol. Pharmacol. 55, 48 (1977).
FASEB 3, 3411 (1989).
FASEB 3, 5256 (1989).
Lancet, 1183, (1978).
J. Am. Chem. Soc. 103, 3215 (1981).
J. Am. Chem. Soc. 104, 6787 (1982).
J. Antibiot. 28, 721-726 (1975).
J. Antibiot. 28, 727-732 (1975).
J. Antibiot. 31, 539-545 (1978).

*Primary Examiner*—C. Warren Ivy
*Assistant Examiner*—Celia Chang
*Attorney, Agent, or Firm*—Arnold S. Milowsky

[57] ABSTRACT

A compound of the structure

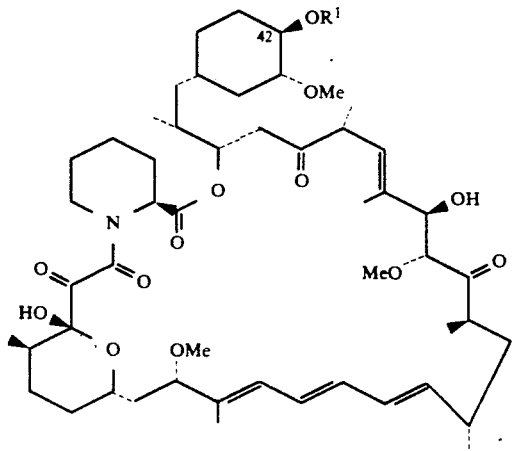

wherein $R^1$ is

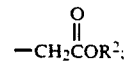

$R^2$ is hydrogen, alkyl of 1-6 carbon atoms, cycloalkyl of 3-8 carbon atoms which is optionally unsaturated, aralkyl of 7-10 carbon atoms, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or a carboxylic acid;

or a pharmaceutically acceptable salt thereof when $R^2$ is hydrogen, which are useful in the treatment of transplantation rejection, host vs. graft disease, autoimmune diseases, diseases of inflammation, or fungal infections.

4 Claims, No Drawings

RAPAMYCIN ALKOXYESTERS

This is a continuation of application Ser. No. 07/598,270 filed Oct. 16, 1990 now abandoned.

BACKGROUND OF THE INVENTION

This invention relates to novel ethers of rapamycin and a method for using them in the treatment of transplantation rejection, host vs. graft disease, autoimmune diseases, diseases of inflammation or fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,929,992; and U.S Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions.

DESCRIPTION OF THE INVENTION

This invention provides derivatives of rapamycin which are useful as immunosuppressive, anti-inflammatory, or antifungal agents having the structure

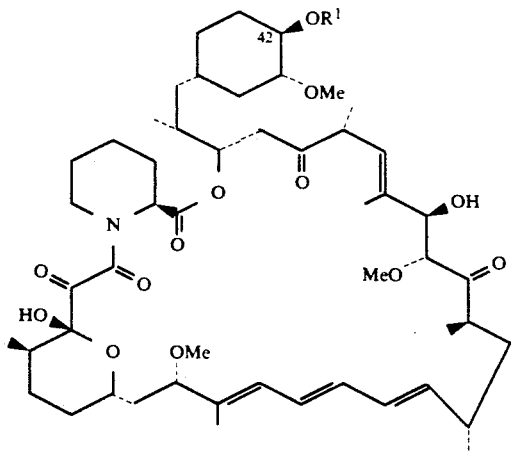

wherein $R^1$ is

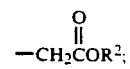

$R^2$ is hydrogen, alkyl of 1–6 carbon atoms, cycloalkyl of 3–8 carbon atoms which is optionally unsaturated, aralkyl of 7–10 carbon atoms, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or a carboxylic acid;

or a pharmaceutically acceptable salt thereof when $R^2$ is hydrogen.

Of the compounds, preferred members are those in which $R^2$ is alkyl of 1–6 carbon atoms.

The pharmaceutically acceptable salts may be formed from inorganic cations such as sodium, potassium, calcium, magnesium and the like or may be in the form of a quaternary ammonium salt.

The compounds of this invention can be prepared by reacting rapamycin with the appropriately substituted ester of diazoacetic acid in the presence of a divalent cation salt, such as rhodium (II) diacetate dimer or copper (II) triflate, as shown below.

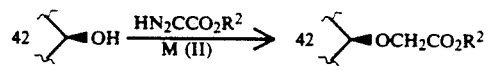

This method of preparing alkoxyesters has been described by B. Ganem et al., J. Am. Chem. Soc. 104, 6787 (1982). The starting materials utilized are either commercially available or can be prepared by methods disclosed in the literature.

The compounds of this invention, rapamycin-42-ethers, provide stability against hydrolysis of the 42-side chain by virtue of the ether moiety connecting the side chain to rapamycin at the 42-position.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the percent inhibition of lymphoproliferation of 1 μM.

$$\frac{{}^3\text{H-control thymus cells} - \text{H}^3\text{-rapamycin-treated thymus cells}}{{}^3\text{H-control thymus cells} - \text{H}^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, as in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d.. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{{}^3\text{H-PLN cells control C3H mouse} - {}^3\text{H-PLN cells rapamycin-treated C3H mouse}}{{}^3\text{H-PLN cells control C3H mouse} - {}^3\text{H-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385-402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1

| Compound | LAF* (ratio) | PLN* (ratio) | Skin Graft (days + SD) |
|---|---|---|---|
| Example 1 | 0.46 | 0.74** | 7.5 ± 1.2 |
| Example 2 | 0.27 | + | + |
| Rapamycin | 1.0 | 1.0 | 12.0 ± 1.7 |

*Calculation of ratios was described supra.
**A result of −0.14 also was obtained for Example 1.
+Not evaluated The results of the LAF standard pharmacological test procedure demonstrates that the compound of Example 2 suppressed T-cell proliferation, and is therefore useful as an immunosuppressive agent. Based on the results of the in vitro and in vivo standard pharmacological test procedures, it was unclear whether the compound of Example 1 had immunosuppressive activity. A ratio of 0.46 in the LAF and 0.74 in the PLN test procedures indicates that the compound of Example 1 suppressed T-cell proliferation; however, the −0.14 ratio that was also obtained in the PLN test procedure could be indicative of immunostimulation.

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth. The results of this test procedure showed that the compounds of this invention have antifungal activity.

TABLE 2*

| | Strain of *Candida albicans* | | | | |
|---|---|---|---|---|---|
| Compound | ATCC 10231 | ATCC 38246 | ATCC 38247 | ATCC 38248 | 3669 |
| Example 1 | 0.5 | 0.1 | 0.2 | 0.1 | 0.05 |
| Example 2 | 0.05 | 0.2 | 0.05 | 0.1 | 0.2 |
| Rapamycin | 0.003 | 0.025 | 0.003 | 0.006 | 0.025 |

*expressed as MIC (μg/ml)

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease; or fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredients is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1–0.5 percent, preferably 2%, of active compound which may be administered to a fungally affected area.

The following examples illustrate the preparation of representative compounds of this invention.

EXAMPLE 1

42-Deoxy-42-(2-ethoxy-2-oxoethoxy)rapamycin

A solution of rapamycin (2.0 g, 2.187 mmol) and rhodium (II) diacetate (37 mg, 0.08 mmol) in benzene (50 mL) was heated to reflux and ethyl diazoacetate (750 mg, 690 μL, 6.56 mmol) in benzene (10 mL) was added over 10 min. The mixture was concentrated and purified by chromatography (silica gel, ethyl acetate-hexane, 1:1) to give 700 mg of product (32%) as a glass. The product was stirred with hexane with the addition of small amounts of ethyl acetate, ether and methylene chloride for 3 d to yield a white powder which was filtered to give 42-deoxy-42-(2-ethoxy-2-oxoethoxy)-rapamycin (496 mg, 23%). The product was isolated as the hemihydrate. IR (KBr) 1680, 1730, 2920, 3430 cm$^{-1}$; $^1$H-NMR (CDCL$_3$)δ1.28 (3H, t, J=7.14 Hz), 1.65 (3H, s), 1.74 (3H, s) 3.14 (3H, s), 3.34 (3H, s), 3.41 (3H, s), 4.20 (2H, q, J=7.14 Hz), 4.30 (2H, dd); Mass Spect (neg. ion FAB) m/z 999 (94%), 590 (15%), 407 (16%), 379 (4%), 253 (6%), 167 (100%).

Analysis Calcd for C$_{55}$H$_{85}$N O$_{15}$•0.5 H$_2$O:C, 65.45; H, 8.59; N, 1.39 Found: C, 65.29; H, 8.64; N, 1.60.

The following representative compounds can be prepared from rapamycin and the appropriately substituted ester of diazoacetic acid by employing the method used to prepare the title compound in Example 1. 42-Deoxy-42-(2-phenoxy-2-oxoethoxy)rapamycin 42-Deoxy-42-[2-(4-chlorophenoxy)-2-oxoethoxy]rapamycin 42-Deoxy-42-(2-phenylmethoxy)-2-oxoethoxy)rapamycin 42-Deoxy-42-(2-cyclobotoxy)-2-oxoethoxy)rapamycin 42-Deoxy-42-[2-(cyclohex-2-enyloxy)-2-oxoethoxy]-rapamycin

EXAMPLE 2

42-Deoxy-42-[2-(1,1-dimethylethoxy)-2-oxoethoxy]-rapamycin

To solution of rapamycin (2.0 g, 2.187 mmol) and rhodium (II) diacetate (20 mg, 0.04 mmol) in methylen chloride (50 mL) was added with t-butyl diazoacetate (750 mg, 690 μL, 6.56 mmol) in methylene chloride (20 mL) over 1.5 h and the reaction mixture was allowed to stir overnight. The mixture was concentrated and purified by chromatography (silica gel, ethyl acetate-hexane, 4:6) to give the product as a glass. The product was dissolved with methylene chloride and concentrated to give the product as a while solid (588 mg, 26%). The product was then dried in vacua at 68° C. overnight and isolated as the hemihydrate. IR (KBr) 1650, 1725, 1750, 2940, 3440 cm$^{-1}$; $^1$H-NMR (CDCL$_3$)δ1.47 (9H, s), 1.65 (3H, s), 1.74 (3H, s), 3.14 (3H, s) 3.34 (3H, s) 3.34 (3H, s), 4.20 (2H, dd); Mass spect (neg. ion FAB) m/z 1027 (32%), 590 (13%), 435 (9%), 167 (100%).

Analysis Calcd for C$_{57}$H$_{89}$N O$_{15}$•0.5 H$_2$O:C, 66.00; H, 8.74; N, 1.35 Found: C, 65.83; H, 8.60; N, 1.29.

What is claimed is:

1. A compound of the structure

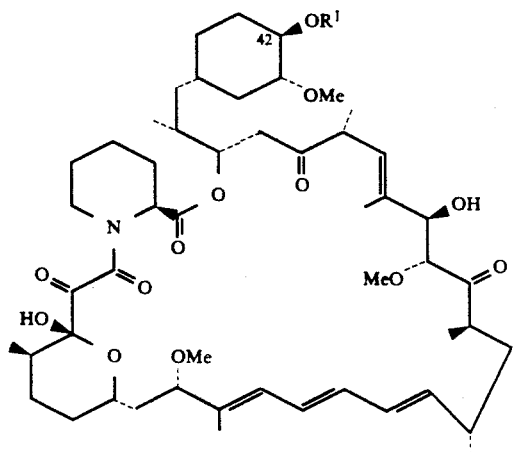

wherein R$^1$ is

R² is hydrogen, alkyl of 1-6 carbon atoms, cycloalkyl of 3-8 carbon atoms which is optionally unsaturated phenylalkyl of 7-10 carbon atoms, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or a carboxylic acid;

or a pharmaceutically acceptable salt thereof when R² is hydrogen.

2. A compound of claim 1 where R² is alkyl of 1-6 carbon atoms.

3. A compound of claim 1 which is 42-deoxy-42-(2-ethoxy-2-oxoethoxy)rapamycin.

4. A compound of claim 1 which is 42-deoxy-42-[2-(1,1-dimethylethoxy)-2-oxoethoxy]-rapamycin.

* * * * *